United States Patent [19]

Steinberg et al.

[11] Patent Number: 5,344,848
[45] Date of Patent: Sep. 6, 1994

[54] PROCESS AND APPARATUS FOR THE PRODUCTION OF METHANOL FROM CONDENSED CARBONACEOUS MATERIAL

[76] Inventors: Meyer Steinberg, 15 Alderfield La., Melville, N.Y. 11747; Yuanji Dong, 125 Terry Rd., Port Jefferson Station, N.Y. 11776

[21] Appl. No.: 68,400

[22] Filed: May 27, 1993

[51] Int. Cl.$^5$ ............................................. C07L 27/06
[52] U.S. Cl. ................................................. 518/704
[58] Field of Search ......................................... 518/704

[56] References Cited

U.S. PATENT DOCUMENTS

| | | | |
|---|---|---|---|
| 3,763,205 | 10/1973 | Green | 260/449.5 |
| 3,940,428 | 2/1976 | Connell et al. | 260/449.5 |
| 4,050,908 | 9/1977 | McNamee et al. | 260/449.5 |
| 4,115,075 | 9/1978 | McNamee et al. | 197/449.6 |
| 4,339,546 | 7/1982 | Randalls | 518/704 |
| 4,395,495 | 7/1983 | Cummings | 158/704 |
| 4,822,935 | 4/1989 | Scott | 585/240 |
| 5,079,267 | 1/1992 | Kao et al. | |

OTHER PUBLICATIONS

Othmer, Kirk—Encyclopedia of Chemical Technology—vol. 15—pp. 398–415 3rd ed, John Wiley, New York.

*Primary Examiner*—Howard T. Mars
*Attorney, Agent, or Firm*—Kelly & Hulme

[57] ABSTRACT

An intergrated recycle process for the production of methanol from a process synthesis gas produced by hydrogasification of a condensed carbonaceous feedstock to produce a process gas which is reacted in a steam pyrolysis reactor with additional natural gas and steam to produce said synthesis gas containing hydrogen and carbon monoxide in more than a 2:1 molar ratio which constituents in turn are reacted in a methanol synthesis reactor to produce methanol. The important factor in this process includes the sequence of reactors of the condensed carbonaceous material: a hydrogasification reactor; the stream and natural gas pyrolysis reactor; the methanol synthesis reactor and the recycling to the hydrogasification reactor of the hydrogen-rich gas stream remaining after the methanol synthesis and separation of the methanol product.

11 Claims, 3 Drawing Sheets

PROCESS AND APPARATUS FOR THE PRODUCTION OF METHANOL FROM CONDENSED CARBONACEOUS MATERIAL

BACKGROUND OF THE INVENTION

1. Field of the Invention

The present invention is related to a method and apparatus for the production of methanol and more specifically to a continuous method and apparatus using condensed carbonaceous raw materials such as coal, natural gas, (i.e.; methane) wood, municipal solid waste, other biomass and other carbonaceous material for such production.

2. Description of the Prior Art

Methanol, which was first discovered in the late 1600's, has found uses as a chemical feedstock, as well as an efficient fuel. Its earliest and largest use to date is as a feedstock in the production of formaldehyde. While in recent years such use has decreased, methanol has found increasing use in the production of such materials as acetic acid and methyl tert-butyl ether (MTBE—a gasoline additive). In addition, methanol is being used directly (with increasing demand) as a fuel in race cars, in farm equipment and, in some areas, as a general purpose automotive fuel.

As will be discussed further below, there are several commercially viable methods of producing methanol. While different feedstocks are used and various processing steps are involved in these methods, they all must produce or otherwise provide carbon monoxide and hydrogen in a molar ratio of 1 mole of CO to 2 moles of $H_2$. These reactants are then reacted in a methanol synthesis reactor to produce methanol in accordance with the following exothermic reaction:

$$CO + 2H_2 \rightarrow CH_3OH$$

The processes known in the art often also produce carbon dioxide which, if fed into the methanol synthesis reactor, results in a lower methanol yielding reaction which competes with the above reaction for the valuable hydrogen as follows:

$$CO_2 + 3H_2 \rightarrow CH_3OH + H_2O$$

The oldest method of producing methanol on a commercially significant scale was the destruction distillation of wood. However, this method is no longer practiced in the United States.

A current conventional source of methanol, which produces approximately ninety (90%) percent of the methanol used, is the conversion of natural gas to methanol. This process involves the catalyzed conversion or reforming of the natural gas with steam to a synthesis gas containing principally carbon monoxide and hydrogen which synthesis gas is subsequently converted to methanol in the presence of a second catalyst. Excess hydrogen is either vented or used as a fuel.

A second method of preparing methanol taught in the art uses condensed carbonaceous material such as fossil fuels, biomass, wood, paper, plastic and the like. This approach involves gasifying the condensed carbonaceous material with steam and oxygen at elevated pressure and temperature to produce hydrogen and carbon monoxide in approximately a 1:1 molar ratio. As discussed above, a 2:1 molar ratio of hydrogen to carbon monoxide is necessary for the production of methanol. In this process, that is accomplished by further reacting some of the carbon monoxide with steam to form the additional hydrogen required to produce methanol. This second step takes place in a shift reactor and also produces carbon dioxide. The gas from the shift reactor must be solvent washed or scrubbed to separate and remove the carbon dioxide, which is vented to the atmosphere, leaving a process gas containing mainly hydrogen and carbon monoxide in a molar ratio of approximately 2 to 1 for feeding to a catalytic methanol convertor, where methanol is produced. Excess gas is either used as fuel or is vented.

While this approach may use a broader class of feed material than the forst process described, it does not achieve high methanol yields per quantity of feedstock and has than desirable thermal and carbon condensed efficiency. Furthermore, the second method requires the shift reaction (an extra step) to produce $H_2/CO$ in the 2:1 molar ratio as needed by the methanol synthesis reactor to maximize the production of methanol per unit of feedstock. In addition, this second process also produces carbon dioxide in large quantities which must be removed prior to entry of the shift reaction products into the methanol synthesis reactor to prevent reduction of the methanol yield. Furthermore, this process also requires pure oxygen for the gasifications reaction which is endothermic.

A more detailed discussion of the above processes can be found in *Kirk-Othmer Encyclopedia of Chemical Technology*, Vol. 15, pp 398–415, John Wiley & Sons (1978).

It is therefore an object of the present invention to provide an efficient method and apparatus for the production of methanol from condensed carbonaceous material.

It is another object of the present invention to provide a method and apparatus for the production of methanol which produces a higher yield of methanol per unit feedstock.

It is another object of the present invention to provide a method and apparatus for the production of methanol with a reduced mass and thermal loss.

It is still another object of the present invention to provide a method and apparatus for the production of methanol which does not require a shift reactor to produce hydrogen and carbon monoxide in a molar ratio of 2:1.

It is yet another object of the present invention to provide a method and apparatus for the production of methanol having reduced carbon dioxide emissions and which eliminates the need for carbon dioxide removal.

It is still another object of the present invention to provide a method and apparatus for the production of methanol which eliminates the need for oxygen.

It is yet another object of the present invention to provide a method and apparatus for the production of methanol which gives a higher yield of methanol per unit of feedstock and has a higher thermal and carbon conversion effeciency than the conventional processes.

The above and other objects and advantages of the present invention will become apparent from the following specification read in conjunction with the annexed drawings.

SUMMARY OF THE INVENTION

This invention relates to the production of methanol by conversion of condensed carbonaceous raw material and the apparatus for same. The process of the present invention is comprised of three steps, the first of which is the hydrogasification of solid and/or liquid carbonaceous materials with hydrogen gas under elevated pressure and temperature to convert the carbonaceous material to a process gas rich in methane and with a low carbon dioxide content. The hydrogasification step is either exothermic or at least thermally neutral and therefore requires no additional input of thermal energy.

The methane-rich process gas from the first step of the process then undergoes steam pyrolysis which is accomplished with the addition of more methane to form a synthesis gas containing higher amounts of carbon monoxide and which is rich in hydrogen. This pyrolysis step takes place in the presence of a catalyst at a higher temperature and either at the same or lower pressure than the hydrogasification step. The steam pyrolysis step is endothermic and requires additional thermal energy input.

Finally, the hydrogen rich and carbon monoxide containing synthesis gas produced in step two is combined by a catalytic reaction in a methanol synthesis reactor at a lower temperature and the same pressure as step one to form methanol. The methanol may then be separated from the product gas stream produced in the methanol synthesis reactor by known fractionating techniques.

An important feature of the present invention is that the hydrogen used in the first step of the process is provided by recycling the product gas stream from the methanol synthesis reactor left after the separation of the methanol. The recycle stream is rich in hydrogen and also contains unused methane. The use of this recycled stream enhances and improves the yield of the hydrogasification step described above and conserves the mass and energy balance of the entire system and thus provides for higher mass and thermal efficiency of the entire process.

The process and apparatus of the present invention may successfully use as a feedstock all condensed carbonaceous materials including fossil fuels such as oil, coal or natural gas; agricultural products such as corn, rice and the like; wood; plant matter; marine plant matter such as seaweed, kelp, marine organisms; waste material such as household garbage, paper, municiple solid waste and the like.

DETAILED DESCRIPTION OF THE INVENTION

Figure 1:
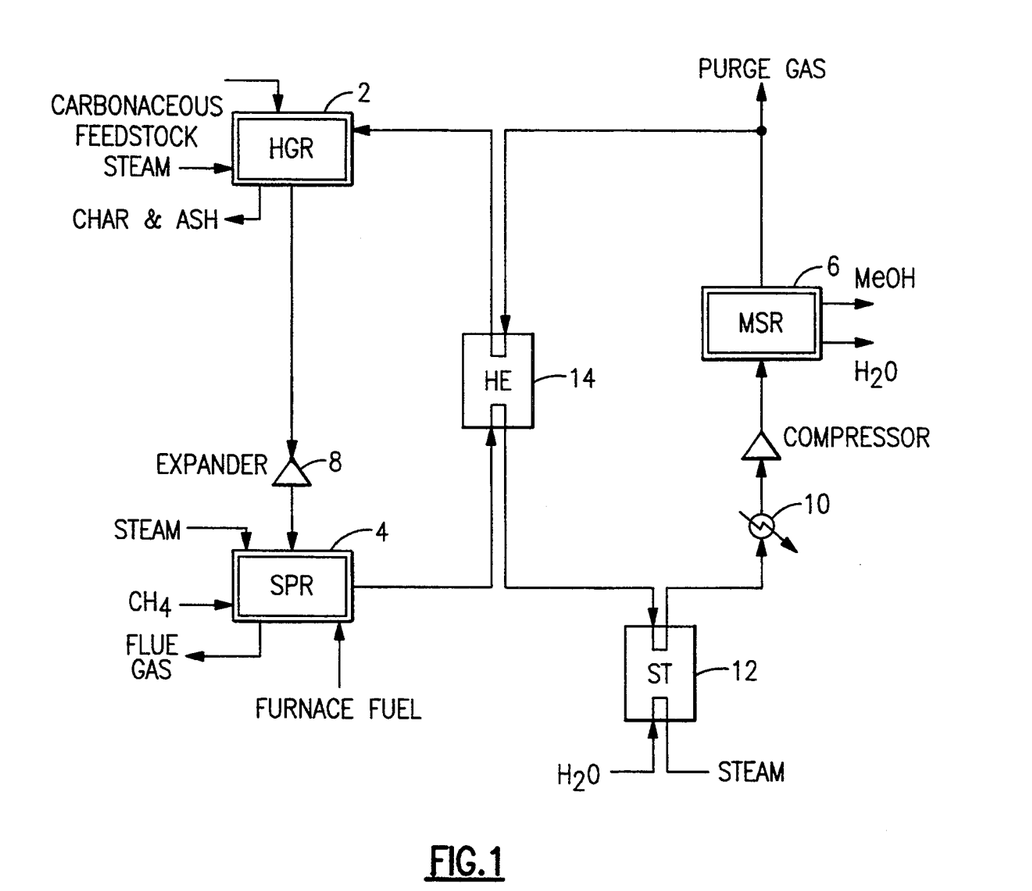
FIG. 1 is a simplified schematic process flow chart of the process of this invention.

Referring to FIG. 1, an embodiment of the overall process is shown which may be divided into three principal sections: Hydrogasification, Steam pyrolysis and Methanol synthesis.

As shown, a solid or liquid carbonaceous material and steam are fed into the hydrogasification reactor 2 along with a recycled hydrogen rich gas. These components are reacted to produce a process gas rich in methane and containing minor amounts of carbon dioxide, and other impurities. The main hydrogasification reactions are exothermic and the entire hydrogasification step, if not exothermic, is at least thermally neutral, Therefore, requires no additional input of energy, In addition, carbon dioxide production is minimized by this approach and therefore no carbon dioxide removal step is required.

This above-described process takes place in a hydrogasification reactor 2 which may be any solid-gas contact reactor but preferably a fluidized bed reactor with particles of the carbonaceous feedstock flowing downward due to gravity balanced by the upward flow of process gas which fluidizes the solid carbonaceous particles. In accordance with the present invention the hydrogasification reactor 2 is operated at a temperature ranging from 700° C. to 900° C. and a pressure which can range from 10 atmospheres to 100 atmospheres. The preferred combination of this temperature and pressure is 800° C. to 900° C. and 30 to 50 atmospheres which combination maximizes the concentration of methane in the process gas produced by this hydrogasification step.

As will be clear to one skilled in the art, the carbonaceous material used in the process of the present invention is one of the sources of the carbon which will eventually be incorporated in the methanol produced by this process. Ideally, the material used will contain between 30% and 80% by weight carbon, the balance being comprised of bonded hydrogen, oxygen and containing water, ash, sulfur, nitrogen and other impurities. Additional elemental carbon, hydrogen and oxygen, as needed, are provided to the hydrogasification reactor 2 by the recycled hydrogen rich steams described below and the additional steam.

In general, the reactions that take place in the hydrogasification reactor 2 and the stoichiometric requirements of such reactions are expressed by the following general equations:

(1) $C + 2H_2 \rightarrow CH_4$ (1)

(2) $C + H_2O \rightarrow CO + H_2$ (2)

(3) $2H_2O + C \rightarrow CO_2 + 2H_2$ (3)

(4) $CO_2 + H_2 \rightarrow CO + H_2O$ (4)

Reactions (1) and (2) are the main reaction occuring in the Hydrogasification reactor 2 with reactions (3) and (4) occuring to a lesser extent. Reaction (4) not only consumes the carbon dioxide produced in reaction (3) but also any carbon dioxide contained in the hydrogen rich recycle stream discussed below. The final composition of the process gas from the hydrogasification reactor is determined by the thermodynamic equilibrium and kenetics among the five (5) gaseous components of said process gas: hydrogen, methane, carbon monoxide, carbon dioxide and water.

The hydrogasification reactions, in addition to producing the above-described products will also (depending on the specific feed stock employed) produce a variety of minor gaseous by-products, such as $H_2S$, as well as some char and ash. The char and ash is removed from the reactor and disposed of properly. The gaseous products remain in the process gas produced by this step, are passed to the next step and contribute to maintaining the overall mass balance of this process.

The carbonaceous feedstock will sometimes contain impurities that will detrimentally impact the catalysts or reactions employed in the present process. If such is the case, additional components may be employed in the hydrogasification reactor 2 to eliminate these impurities. For example, if any sulfur containing coal is employed in the feedstock the sulfur, which may "poison" the catalysts used in subsequent steps, must be removed. This is typically accomplished by the addition of limestone to the hydrogasification reactor 2 which reacts with the sulfur to produce a product easily removed along with the char and ash.

The overall hydrogasification process is either exothermic or, at least, thermally neutral. Therefore, no additional thermal energy is needed in this reactor. As a result of the exothermic nature of the overall reactions, no oxygen (which is typically required in a conventional gasification reactor since the reaction is endothermic and thus thermal energy is needed) is required. Furthermore, the carbon dioxide production in the hydrogasification reactor 2 is minimized. Depending on the carbonaceous feedstock used, the process gas produced by the hydrogasification reactor 2 usually contains five (5) significant gaseous components: hydrogen, methane, carbon monoxide, carbon dioxide and steam; approaching equilibrium amounts, the major gas component being methane which can vary in the range 20% to 50% by volume.

As described above, the process of the present invention is a continuous process. In the hydrogasification reactor 2, the residence time of the solid phase (i.e. the time a particle of carbon in the condensed carbonaceous feedstock remains in a solid phase in the reactor) can range from five (5) minutes for biomass to one (1) hour for coal, the preferred residence time being in the range of 10 to 30 minutes.

As will be clear to one skilled in the art, the purpose behind the reaction in the hydrogasification reactor 2 is to produce methane and also to begin to form carbon monoxide which is required in a subsequent step of the process of the present invention. While this goal may be achieved without the introduction of steam into the hydrogasification reactor 2 [see reaction equation (1) above], the presence of the steam produces additional carbon monoxide [see reaction equation (2) above] and aids in the maximum conversion of carbon in the feedstock.

The hydrogasification reactor process gas is next passed through an expander 8 which reduces the pressure and temperature of the process gas which is then fed into a steam pyrolysis reactor 4 for the next step of the process. This next step takes place in a steam pyrolysis reactor 4 which has similarities to a conventional steam reformer of natural gas.

The steam pyrolysis reactor 4 is comprised of a tubular heat exchanger set into a heated gas furnace. The gas furnace is at low atmospheric pressure. The process gas flows inside the heat exchanger tubes and is heated by the heat transfer through the tube walls by the hot furnace gases. As further described below, this step requires a catalyst which is packed inside the heat exchanger tubes so that as the process gas passes through the steam pyrolysis reactor 4 it passes through and in contact with the catalyst.

The steam pyrolysis reactor 4 may operate in the range of 800° C. to 1200° C. and at a pressure in the range of 10–100 atmosphere with 1000° C. and 30 atmospheres being the preferred operating conditions. The residence time of the process gas within the reactor is relatively short and depends on the heat flux in the reactor tubes, the residence time of less than 10 seconds being typical to establish equilibrium of the reaction gases in the steam pyroysis reactor 4.

As indicated above, the methane rich process gas stream from the hydrogasification reactor 2 is fed into the steam pyrolysis reactor 4 and while there is steam and a significant amount of methane contained in this process gas, additional steam and methane is provided to the steam pyrolysis reactor 4 from an external source to provide for establishing equilibrium conditions of the reactants in the steam pyrolysis reactor 4. The major reaction that takes place in the steam pyrolysis reactor 4 is described as follows:

(5) $H_2O + CH_4 \rightarrow CO + 3H_2$ \hfill (5)

As described above, the steam used in this reaction is provided by the steam content of the process gas from the hydrogasification step and the steam addition from an external source. While there are other side reactions and products passing through the steam pyrolysis reactor 4, the main and desired products of the reactor 4 is a synthesis gas containing carbon monoxide and which is rich in hydrogen.

The composition of the synthesis gas produced by the the steam pyrolysis reactor 4 is controlled by the approach to thermodynamic equilibrium of the gaseous components: hydrogen, carbon monoxide, carbon dioxide, methane and steam at the pressure and temperature conditions of reactor 4. The ratio of hydrogen and carbon monoxide (the major constituents of the synthesis gas stream) is greater than a 2 to 1 molar ratio and can range from 2.5 to 1 up to 6.5 to 1 and in a preferred molar ratio of between 2.5 and 4.5. The carbon monoxide and hydrogen typically form approximately 80% or more of the the volume of the synthesis gas stream produced by pyrolysis reactor 4.

The steam pyrolysis reaction is endothermic and requires thermal energy input which as discussed above is provided by a gas fired furnace. The combustion gases typically employed to provide the thermal energy is a mixture of natural gas (methane), purge gas and air.

The above-described steam pyrolysis reaction is usually performed in the presence of a catalyst in order to improve the rate of reaction to approach thermodynamic equilibrium values for the reactions seen in the reactor. Suitable catalysts include any of the metal oxide class catalyst and preferably include nickel oxide based catalysts.

In the third step of this process, the carbon monoxide and hydrogen containing synthesis gas produced in step two are reacted in a methanol synthesis reactor 6 operated at approximately 50 atmospheres and 260° C. by a catalyzed reaction to produce methanol in accordance with the following major reaction (6) and minor (due to low $CO_2$ content of the synthesis gas) reaction (7):

(6) $CO + 2H_2 \rightarrow CH_3OH$ \hfill (6)

(7) $CO_2 + 3H_2 \rightarrow CH_3OH + H_2O$ \hfill (7)

A suitable catalyst for this reaction is any one which will facilitate the above reaction at a suitable rate at the above recited reaction temperature and pressure, while reducing any side reactions that would reduce the methanol production. The most often used catalyst in the process is the well known Cu/Zn based catalyst (ICI low pressure catalyst).

The gaseous output of the methanol synthesis reactor, in addition to containing methanol, contains significant quantities of other gaseous components such as water, unreacted carbon monoxide, carbon dioxide, methane, and the like, and is rich in hydrogen. However, since the boiling point of the methanol (and water) is significantly higher than the other components the methanol and water are easily separated from the output gases and are further separated from each other, by techniques known in the art such as condensation and fractionation, to produce concentrated methanol.

As indicated above, the product gas stream remaining after the removal of methanol is rich in unreacted hydrogen. Furthermore, as described relative to the hydrogasification reaction, hydrogen is an important and necessary reactant introduced to the hydrogasification reactor 2 for reaction with the carbonaceous feedstock. Since hydrogen is available from the product stream from the methanol sythesis reactor 6, in accordance with the present invention this hydrogen rich product stream may be recycled to the hydrogasification reactor 2 so that no external source of hydrogen is neccessary. In addition, the other component of the recycled product stream help maintain the overall mass balance of the process.

It will be clear to one skilled in the art and as depicted in FIG. 1, a certain amount of the recycled stream must be vented from the process to purge the system of inert gases such as nitrogen which may build up and dilute the process gases. This is referred to as purge gas.

The process gas stream emerging from the steam pyrolysis reactor 4 must have a substantial reduction in temperature prior to its being fed into the methanol synthesis reactor 6. While this heat may be discharged to outside cooling water or the atmosphere, in accordance with the present invention this gas stream may be fed to the high temperature side of a heat exchanger 14 with the recycled gas discussed above being fed to the low temperature side of said heat exchanger 14 which will partially reduce the temperature of the steam pyrolysis reactor gas stream and also increase the temperature of the recycled stream to the operating temperature of the hydrogasification reactor. This partially temperature reduced gas stream may then be fed through another heat exchanger 12 to further reduce the temperature of the process gas feed fed into the methanol synthesis reactor 6. The heat extracted by the heat exchanger 12 can be used to produce steam which can be used as a feed to the hydrogasification reactor 2 and the steam pryolysis reactor 4, or for generation of power in a steam driven turbogenerator.

If required, a compressor unit 10 is provided after the beat exchanger 12 to raise the pressure of the process gas to the pressure required by the methanol synthesis reactor 6.

Figure 2:
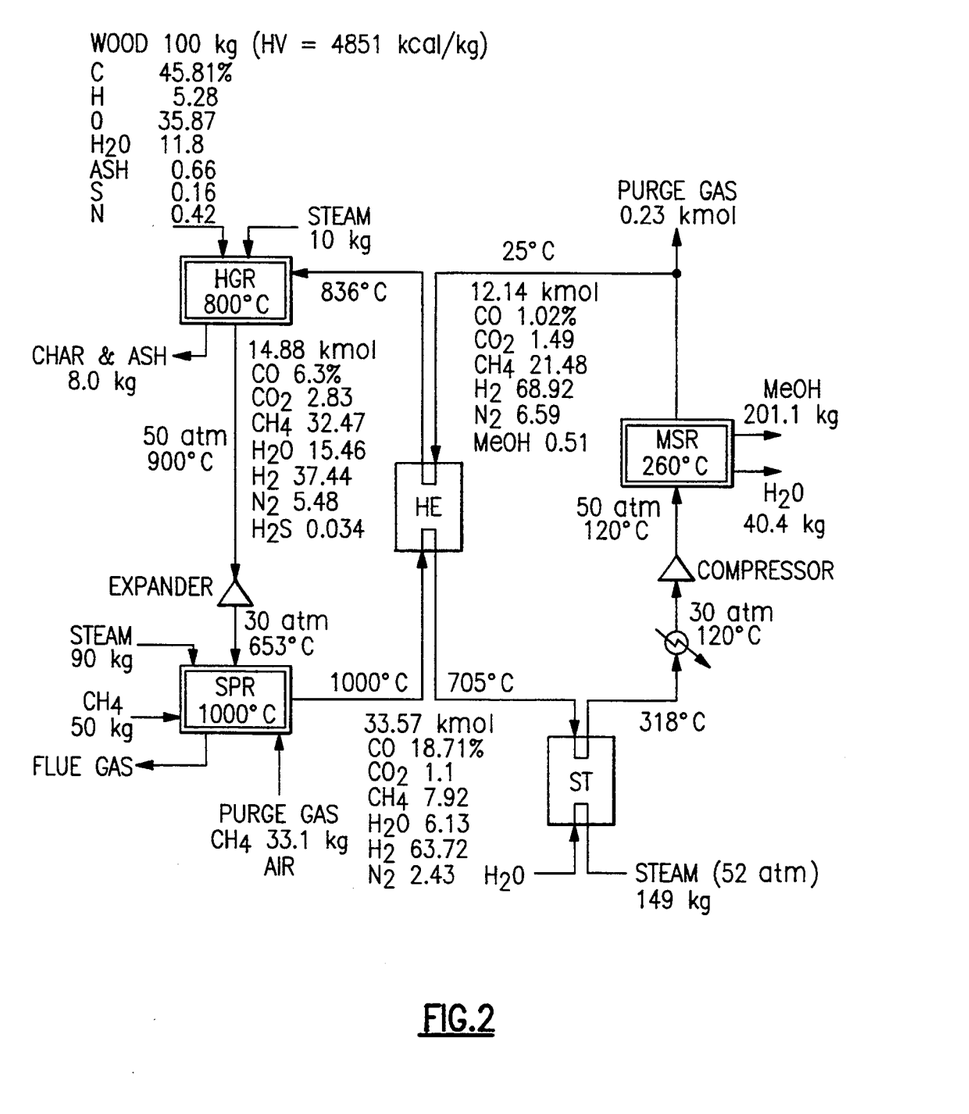
FIG. 2 shows computer simulated results of the process of the present invention with biomass and natural gas as feedstock.
Figure 3:
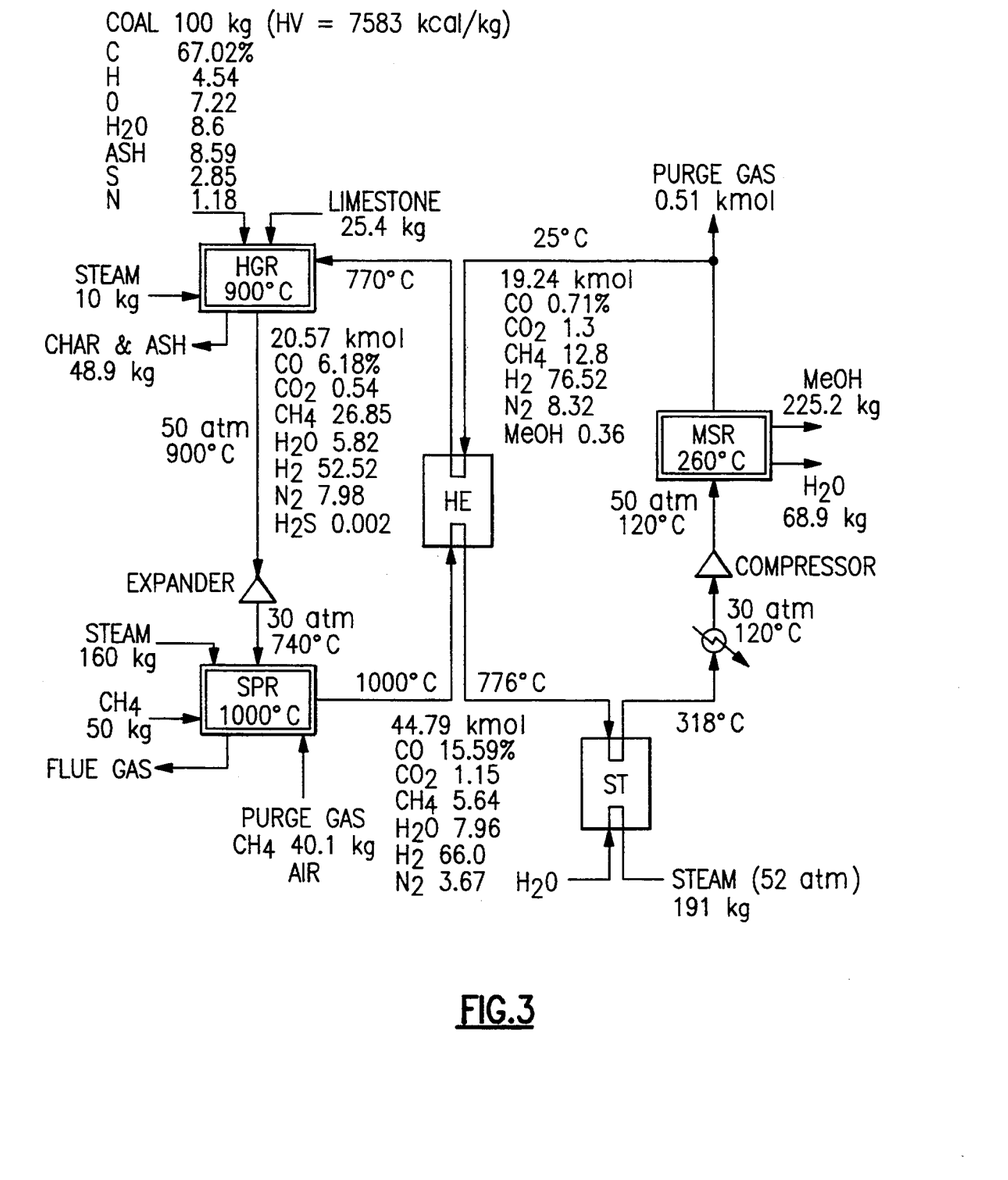
FIG. 3 shows another computer simulated result of the process of the present invention with coal and natural gas as the feedstock.

The process of the present invention is illustrated by computer process simulations, the results of which are shown in FIGS. 2 & 3. These simulations were run assuming standard thermodynamic equilibrium data for the five gaseous constituents seen in the present process: hydrogen, methane, carbon monoxde, carbon dioxide and water and in equilibrium with condensed carbon species in the hydrogasification reactor 2. In addition to these computer simulations of the process of the present invention, actual tests were performed in the laboratory to verify the simulation results and to obtain rate data.

The process of the present invention is exemplified by the following examples generated by the above-discussed simulation. In interpreting the results of these examples the following definitions are given:

$$\text{Thermal Efficiency} = \frac{\text{Heating value of product methanol}}{\substack{\text{Heating value of carbonaceous} \\ \text{feedstock and natural gas} \\ \text{(both feedsstock and fuel)}}}$$

$$\substack{\text{Carbon} \\ \text{Conversion Efficiency}} = \frac{\text{Carbon content of product methanol}}{\substack{\text{Carbon content of carbonaceous} \\ \text{feedstock and natural gas}}}$$

$$CO_2 \text{ Emmision} = \frac{\text{weight of } CO_2 \text{ generated}}{\text{Heating value of methanol produced}}$$

$$HGR \text{ Carbon Conversion} = \frac{\text{Carbon gasified in hydrogasifier}}{\substack{\text{Total carbon} \\ \text{in the carbonaceous feedstock}}}$$

It should also be noted that, since the present process is continuous, the data given in the following examples is on a unit feedstock and unit rate basis; i.e.; 100 kg wood per unit time or 100 kg coal per unit time.

EXAMPLE 1

Using the apparatus described above and shown in FIG. 1, the process of the present invention was simulated using wood as the carbonaceous feedstock. Referring to FIG. 2, it can be seen that the feedstock fed into the hydrogasification reactor is 100 kg wood with 10 kg. steam and 12.14 kmol of a recycle stream containing 21.48% by volume methane and 68.92% by volume hydrogen gas and is operated at the conditions as specified in FIG. 2 at 800° C. temperature and 50 atmospheres. The steam pyrolysis reactor is operated at 30 atmospheres and 1000° C. and the methanol synthesis reactor is operated at 50 atmospheres and 260° C.

With the feedstocks and conditions indicated in FIG. 2, 201.1 kg of methanol are produced. The embodiment, as shown in FIG. 2, has an HGR carbon conversion of 84% and overall carbon conversion efficiency of 69.8%, a thermal efficiency of 71.3% and a carbon dioxide emission of 103 lbs $CO_2$/MMBTU of methanol.

EXAMPLE II

Referring to FIG. 3, it can be seen that the feedstock fed into the hydrogasification reactor is 100 kg coal, 10 kg of steam and 19.24 kmol of a recycle stream containing 12.8% by volume methane and 76.52% by volume hydrogen gas and is operated at the conditions as specified in FIG. 3 at 900° C. temperature and 50 atmospheres pressure. The steam pyrolysis reactor is operated at 30 atmospheres and 1000° C. and the methanol synthesis reactor at 50 atmospheres and 260° C. Additives such as limestone are added to the hydrogasification reactor to remove contaminants such as sulfur which would affect catalysts used in the process.

With the feedstocks and conditions indicated in FIG. 3, 225.2 kg of the methanol is produced. The embodiment as shown in FIG. 3 has an HGR carbon conversion efficiency of 68% and an overall carbon conversion of 62.8%, a thermal efficiency of 64.6% and a carbon dioxide emission of 192 lbs $CO_2$/MMBTU of the methanol thermal energy.

As will be clear to those skilled in the art, the present invention relates to using both condensed carbonaceous materials and methane to produce methanol. Suprisingly, this combined process produces more methanol than that which would be produced from each of the conventional processes operating separately on each of the above feedstocks. This fact is demonstrated by the results shown in attached tables.

TABLE 1 gives typical examples of process parameters successfully used in accordance with the present invention for both biomass/methane and coal/methane feedstocks. TABLES 2 and 3 compare the processes of the present invention with the above described conventional process in two ways: (1) when the conventional plant handles each feedstock alone and (2) when both feedstocks are fed together into a single conventional steam-oxygen gasification plant or steam gasification plant.

By comprising the results detailed in TABLES 1, 2 & 3, it can be seen that the three step recycling process of the present invention produces from at least 15% to 40% higher yields of methanol per unit of natural gas and per unit of biomass feedstock than the optimum conventional steam reforming or gasification process for each of the feedstock alone or in a combined conventional steam reforming process. Also the carbon dioxide emission from this new process is from about 15% to as high as 50% less than $CO_2$ emission from the conventional plants.

Table 2 indicates that a biomass/natural gas process operated in accordance with the present invention produces over three (3) times more methanol per unit of biomass and 1.5 times more methanol per unit of methane than each of the best conventional plants, 15.3% more methanol than two (2) conventional plants each operating on the same quantity of feedstock. Furthermore, the carbon dioxide emmision is 22.7% less for this process than for the conventional.

Table 3 shows that for a coal and natural gas process operated in accordance with the present invention, the methanol yield per unit of coal is over 4 times greater than the yield of a conventional coal conversion plant and 1.6 times per unit of natural gas than that of a conventional plant, and this process produces 18.1% greater yield than two separate conventional plants.

The process of the present invention has the following beneficial features for production of methanol from condensed carbonaceous materials compared to the conventional processes:

1. There is no oxygen plant.
2. There is no shift reactor.
3. The hydrogasification reactor can be designed to be energy neutral since the basic hydrogasification reaction of hydrogen with condensed carbonaceous material is exothermic.
4. The two consecutive steps of hydrogasification followed by steam pyrolysis in accordance with the present invention yields a higher carbon monoxide yield than the conventional process from which methanol is produced.
5. The process of the present invention is totally intergrated which makes maximum use of the mass of the feedstock, minimizes heat losses, and maximizing energy utilization.

TABLE 1

| FEEDSTOCK | | BIOMASS/CH4 | COAL/CH4 |
|---|---|---|---|
| Pressure | HGR (atm) | 50 | 50 |
| | SPR (atm | 30 | 30 |
| Temp | HGR (C) | 800 | 900 |
| | SPR (C) | 1000 | 1000 |
| | MSR (C) | 260 | 260 |
| Dry feedstock (kg) | | 88.2 | 91.4 |
| moisture (kg) | | 11.8 | 8.6 |
| CH4 to SPR (kg) | | 50.0 | 50.0 |
| as fuel (kg) | | 33.1 | 40.1 |
| total (kg) | | 83.1 | 90.1 |
| Steam to HGR (kg) | | 10 | 10 |
| to SPR (kg) | | 90 | 160 |
| total (kg) | | 100 | 170 |
| Steam Maked (kg) | | 149 | 191 |
| HGR Convers. (%) | | 84.1 | 68.3 |
| MeOH (kg) | | 201.1 | 225.2 |
| MeOH/Wood (kg/kg) | | 2.28 | |
| MeOH/Coal (kg/kg) | | | 2.46 |
| MeOH/CH4 (kg/kg) | | 2.42 | 2.50 |
| MeOH/Feed (kg/kg) | | 1.17 | 1.24 |
| G/MeOH (kmol/kg) | | 0.07 | 0.09 |
| Carbon eff. (%) | | 69.8 | 62.8 |
| Thermal eff. (%) | | 71.3 | 64.6 |
| CO2 (lb/MMBTU) | | 102 | 192 |
| Gas temp. to HGR (c) | | 836 | 770 |

HGR—Hydrogasification Reactor
SPR—Steam Pyrolysis Reactor
MSR—Methanol Synthesis Reactor

TABLE 2

| | | Conventional Process | | | |
|---|---|---|---|---|---|
| Factor | Present Invention | BM Gasifi. | NG Reform. | BM/NG Gasf. | BM/NG** Gasf./Refm. |
| Feedstock | | | | | |
| DAF Wood, kg | 88.2 | 88.2 | | 88.2 | 88.2 |
| CH4, kg | 83.1 | — | 83.1 | 83.0 | 83.7 |
| O2, kg | — | 44.1 | — | 100.0 | — |
| Theraml Eff., % | 71.3 | 52.4 | 64.0 | 51.0 | 61.0 |
| Carbon Conv., % | 69.8 | 38.0 | 78.0 | 49.9 | 59.8 |
| Methanol yield | | | | | |
| kg MeOH/kg Wood | 2.28 | 0.51 | — | 1.63 | 1.96 |
| kg MeOH/kg CH4 | 2.42 | — | 1.56 | 1.73 | 2.07 |
| kg MeOH/kg total | 1.17 | — | — | 0.79 | 1.01 |
| MeOH Product, kg | 201 | 44.8 | 129.6 | 143.8 | 173.0 |
| Total, kg | 201 | 174.4 | | 143.8 | 173.0 |
| % increased MeOH by Hynol over conv. processes | — | 15+ | | 38 | 16 |
| CO2 emmision, lb/MMBTU | 103 | 132 | | 150 | 121 |
| % reduced CO2 by Hynol compared to | | 22+ | | 150 | 121 |

TABLE 2-continued

|  | Present Invention | Conventional Process | | | |
|---|---|---|---|---|---|
| Factor | | BM Gasifi. | NG Reform. | BM/NG Gasf. | BM/NG** Gasf./Refm. |
| conv. processes | | | | | |

*Wood and natural gas are gasified with oxygen at 1000° C. The exit gas of the gasifier then goes through the shift reactor and the methanol synthesis reactor. The off gas is used as fuel for oxygen plant.
**Wood and natural gas are gasified with steam at 800° C. The exit gas of the gasifier then goes through the steam reforming reactor (1000° C.) and the methanol synthesis reactor. The off gas is used as one of the fuels for both gasification and steam reforming.
+ Process of the present invention produces (201.1 − 174.4) × 100/174.4 = 15.3% more methanol than two separate conventional processes do.
++ Process of the present invention (132 − 103) × 100/132 = 22% of $CO_2$ emission, compared with two separate conventional processes.

TABLE 3

|  | Present Invention | Conventional Process | | | |
|---|---|---|---|---|---|
| Factor | | Coal Gasifi. | NG Reform. | Coal/NG Gasf. | Coal/NG** Gasf./Refm. |
| Feedstock | | | | | |
| DAF Coal, kg | 91.4 | 91.4 | | 91.4 | 91.4 |
| CH4, kg | 90.1 | — | 89.0 | 90.0 | 89.1 |
| O2, kg | — | 73.1 | — | 120.0 | — |
| Theraml Eff., % | 64.6 | 50.8 | 64.0 | 46.9 | 53.6 |
| Carbon Conv., % | 62.8 | 25.1 | 78.0 | 45.6 | 52.0 |
| Methanol yield | | | | | |
| kg MeOH/kg Coal | 2.46 | 0.57 | — | 1.79 | 2.03 |
| kg MeOH/kg CH4 | 2.50 | — | 1.56 | 1.81 | 2.08 |
| kg MeOH/kg total 1.24 | — | — | 0.86 | 1.03 | |
| MeOH Product, kg | 225 | 51.9 | 138.8 | 163.3 | 185.7 |
| Total, kg | 225 | | 190.7 | 163.3 | 185.7 |
| % increased MeOH by Hynol over conv. processes | — | 18+ | | 38 | 21 |
| CO2 emmision, lb/MMBTU | 190 | 362 | | 264 | 229 |
| % reduced CO2 by Hynol compared to conv. processes | | 48++ | | 28 | 17 |

*Coal and natural gas are gasified with oxygen at 1000° C. The exit of gas of the gasifier then goes through the shift reactor and the methanol synthesis reactor. The off gas is used as fuel for oxygen plant.
**Coal and natural gas are gasified with steam at 900° C. The exit gas of the gasifier then goes through the steam reforming reactor (1000° C.) and the methanol synthesis reactor. The off gas is used as one of the fuels for both gasification and steam reforming.
+ Process of the present invention produces (225.2 − 190.7) × 100/190.7 = 18.1% more methanol two separate conventional processes do.
++ Process of the present invention reduces (362 − 190) × 100/362 = 47.5% of CO2 emmision, compared with two separate conventional processes.
NG Natural Gas

What is claimed is:

1. An intergrated recycle process for the production of methanol from a condensed carbonaceous feedstock selected from the group consisting of coal, biomass, wood, agricultural products and municipal solid wastes comprising:
    a) hydrogasifying said feedstock in a hydrogasification reactor with a recycled hydrogen rich gas stream to produce a process gas stream rich in methane;
    b) steam pyrolyzing said process gas stream in a second stage steam pyrolysis reactor in the presence of a catalyst to produce a synthesis gas containing mainly carbon monoxide and hydrogen with small amounts of carbon dioxide;
    c) reacting said carbon monoxide and hydrogen synthesis gas in a third stage methanol synthesis reactor in the presence of a catalyst to form a product gas stream containing methanol;
    d) removing said methanol from said product gas stream leaving product gas stream rich in hydrogen; and
    e) recycling said hydrogen rich product gas stream to supply the hydrogen needs for the above hydrogasifying step.

2. The process of claim 1 further comprising the steps of:
    a) recovering thermal energy from synthesis gas stream exiting the steam pyrolysis reactor for use in the present process.

3. The process of claim 1 wherein the hydrogasifying step includes the introduction of steam into the hydrogasification reactor.

4. The process of claim 3 wherein the molar ratio of hydrogen to carbon monoxide in the said synthesis gas is greater than 2 to 1 and as high as 6 to 1.

5. The process of claim 1 wherein the steam pyrolysis reactor catalyst is a nickel based catalyst.

6. The process of claim 1 wherein the methanol synthesis reactor catalyst is a copper based catalyst.

7. The process of claim 1 wherein said hydrogasification reactor is operated at a temperature in the range of 700° C. to 900° C. and a pressure range of 10 atmosphere to 100 atmosphere.

8. The process of claim 1 wherein said steam pyrolysis reactor is operated at a temperature in the range of 900° C. to 1200° C. and a pressure range of 10 atmosphere and 100 atmosphere.

9. The process of claim 1 comprising the further steps of:

a) expanding the process gas stream produced by the hydrogasification reactor to decrease its pressure and temperature prior to pyrolyzing said process gas stream; and b) compressing said synthesis gas stream to adjust the temperature and pressure thereof to that needed by the methanol synthesis reactor.

10. The process of claim 9 further comprises the step of purging the inert gases from the process.

11. The process of claim 10 further comprising the step of removing catalyst poisoning impurities from the process prior to feeding any reactants to the pyrolysis reactor.

* * * * *